United States Patent
O'Malley et al.

(10) Patent No.: US 8,518,077 B2
(45) Date of Patent: Aug. 27, 2013

(54) SYSTEM AND METHOD FOR MOVING AND STRETCHING PLASTIC TISSUE

(75) Inventors: Michael T. O'Malley, Appleton (CA); Michael S. G. Bell, Ottawa (CA); James Lee, Almonte (CA); Leonard G. Lee, Almonte (CA)

(73) Assignee: Canica Design Inc., Ottawa, Ontario (CA)

( * ) Notice: Subject to any disclaimer, the term of this patent is extended or adjusted under 35 U.S.C. 154(b) by 1041 days.

(21) Appl. No.: 12/198,033

(22) Filed: Aug. 25, 2008

(65) Prior Publication Data

US 2008/0312685 A1    Dec. 18, 2008

Related U.S. Application Data

(62) Division of application No. 10/275,760, filed as application No. PCT/IB01/00796 on May 9, 2001, now Pat. No. 7,429,265.

(60) Provisional application No. 60/249,766, filed on Nov. 17, 2000, provisional application No. 60/202,739, filed on May 10, 2000.

(51) Int. Cl.
*A61B 17/08*    (2006.01)

(52) U.S. Cl.
USPC .............. 606/215; 606/216; 606/213

(58) Field of Classification Search
USPC .................................. 606/213–218
See application file for complete search history.

(56) References Cited

U.S. PATENT DOCUMENTS

| | | | |
|---|---|---|---|
| 261,531 A | 7/1882 | Cook | |
| 355,092 A | 12/1886 | Knapp | |
| 363,538 A | 5/1887 | Penny | |
| 563,833 A | 7/1896 | Zahl | |
| 667,939 A | 2/1901 | Frye | |
| 701,313 A | 6/1902 | Duffy | |
| 1,074,413 A | 9/1913 | De Baun | |
| 1,434,723 A | 11/1922 | Triay | |
| 1,969,188 A * | 8/1934 | Spicer | 606/216 |
| 2,018,517 A | 10/1935 | Fetter | |
| 2,196,296 A | 4/1940 | Flynn | |
| 2,387,131 A | 10/1945 | Gomez | |
| 2,586,488 A | 2/1952 | Smith | |

(Continued)

FOREIGN PATENT DOCUMENTS

| | | |
|---|---|---|
| CN | 2676918 Y | 2/2005 |
| DE | 10138793 | 2/2003 |

(Continued)

OTHER PUBLICATIONS

European Patent Application No. 06759744.3, Office Action dated Jan. 21, 2010.

(Continued)

*Primary Examiner* — Darwin Erezo
(74) *Attorney, Agent, or Firm* — Kilpatrick, Townsend & Stockton LLP; John S. Pratt; Camilla C. Williams

(57) ABSTRACT

A system and method of moving and stretching plastic tissue using dynamic force. An elastomeric driver is adjustably attachable to one or more anchors for securing the elastomer to the plastic tissue, providing a self adjusting system that is capable of exerting relatively constant tension over a certain distance.

15 Claims, 11 Drawing Sheets

(56) References Cited

U.S. PATENT DOCUMENTS

| | | | |
|---|---|---|---|
| 2,751,909 A | 6/1956 | Weitzner | |
| 2,845,925 A | 8/1958 | Gaetan | |
| 2,887,005 A | 5/1959 | Fromm | |
| 3,402,716 A | 9/1968 | Baxter | |
| 3,454,011 A * | 7/1969 | Wagner | 606/224 |
| 3,520,306 A | 7/1970 | Gardner et al. | |
| 3,698,395 A | 10/1972 | Hasson | |
| 3,762,401 A | 10/1973 | Tupper | |
| 3,762,418 A * | 10/1973 | Wasson | 606/226 |
| 3,783,873 A | 1/1974 | Jacobs | |
| 3,823,709 A | 7/1974 | McGuire | |
| 3,926,193 A * | 12/1975 | Hasson | 606/218 |
| 3,976,079 A | 8/1976 | Samuels et al. | |
| 3,998,217 A | 12/1976 | Trumbull et al. | |
| 4,430,991 A | 2/1984 | Darnell | |
| 4,531,521 A | 7/1985 | Haverstock | |
| 4,535,772 A * | 8/1985 | Sheehan | 606/218 |
| 4,539,990 A | 9/1985 | Stivala | |
| 4,605,005 A | 8/1986 | Sheenan | |
| 4,693,236 A | 9/1987 | Leprevost | |
| 4,742,826 A | 5/1988 | McLorg | |
| 4,780,168 A | 10/1988 | Beisang et al. | |
| 4,825,866 A | 5/1989 | Pierce | |
| 5,009,663 A | 4/1991 | Broome et al. | |
| 5,013,243 A | 5/1991 | Tanaka et al. | |
| 5,029,371 A | 7/1991 | Rosenblood et al. | |
| 5,036,866 A | 8/1991 | Eldrige, Jr. et al. | |
| 5,041,129 A | 8/1991 | Hayhurst et al. | |
| 5,111,558 A | 5/1992 | Ridley et al. | |
| 5,123,843 A | 6/1992 | Van der Zel et al. | |
| 5,127,412 A * | 7/1992 | Cosmetto et al. | 128/898 |
| 5,195,538 A | 3/1993 | Eldridge, Jr. et al. | |
| 5,234,462 A * | 8/1993 | Pavletic | 606/215 |
| 5,259,835 A | 11/1993 | Clark et al. | |
| 5,263,971 A | 11/1993 | Hirshowitz et al. | |
| 5,269,809 A | 12/1993 | Hayhurst et al. | |
| 5,336,219 A | 8/1994 | Krantz | |
| 5,384,103 A | 1/1995 | Miller | |
| 5,406,838 A | 4/1995 | Miller | |
| 5,487,889 A | 1/1996 | Eckert et al. | |
| 5,507,775 A | 4/1996 | Ger et al. | |
| 5,534,010 A | 7/1996 | Peterson | |
| 5,538,500 A | 7/1996 | Peterson | |
| 5,546,961 A | 8/1996 | Harrison | |
| 5,580,344 A | 12/1996 | Hasson | |
| 5,593,379 A | 1/1997 | Rayman | |
| 5,628,724 A | 5/1997 | Debusk et al. | |
| 5,639,244 A | 6/1997 | Stricklin | |
| 5,649,960 A | 7/1997 | Pavletic | |
| 5,662,326 A | 9/1997 | Gebran | |
| 5,665,108 A * | 9/1997 | Galindo | 606/215 |
| 5,681,579 A | 10/1997 | Freeman | |
| 5,778,824 A | 7/1998 | Musgrave et al. | |
| 5,820,578 A | 10/1998 | Johansen | |
| 5,821,000 A | 10/1998 | Inui et al. | |
| 5,843,123 A * | 12/1998 | Brazeau | 606/213 |
| 5,871,357 A | 2/1999 | Tseng | |
| 5,876,333 A | 3/1999 | Bigliani et al. | |
| 5,927,022 A | 7/1999 | Hirakawa et al. | |
| 5,968,097 A * | 10/1999 | Frechet et al. | 623/15.12 |
| 5,972,022 A | 10/1999 | Huxel | |
| 6,066,160 A * | 5/2000 | Colvin et al. | 606/232 |
| 6,102,854 A | 8/2000 | Cartier et al. | |
| 6,106,544 A | 8/2000 | Brazeau | |
| 6,119,318 A | 9/2000 | Maurer | |
| 6,149,669 A | 11/2000 | Li | |
| 6,174,323 B1 | 1/2001 | Biggs et al. | |
| 6,190,312 B1 | 2/2001 | Fowler, Jr. | |
| 6,219,891 B1 | 4/2001 | Maurer et al. | |
| 6,267,744 B1 | 7/2001 | Roberts et al. | |
| 6,329,564 B1 | 12/2001 | Lebner | |
| 6,478,656 B1 | 11/2002 | Khouri | |
| 6,517,563 B1 | 2/2003 | Paolitto et al. | |
| 7,361,185 B2 | 4/2008 | O'Malley et al. | |
| 7,429,265 B2 | 9/2008 | O'Malley et al. | |
| 2005/0020957 A1 | 1/2005 | Lebner | |
| 2005/0085757 A1 | 4/2005 | Santanello | |
| 2005/0182443 A1 | 8/2005 | John et al. | |
| 2008/0147115 A1 | 6/2008 | O'Malley et al. | |

FOREIGN PATENT DOCUMENTS

| | | |
|---|---|---|
| EP | 296669 | 6/1987 |
| EP | 279534 | 8/1988 |
| EP | 792622 | 2/1997 |
| FR | 2661821 | 11/1991 |
| GB | 328741 | 5/1930 |
| GB | 2188850 | 10/1987 |
| GB | 2215771 | 9/1989 |
| WO | WO-92/15251 | 9/1992 |
| WO | WO-9317633 | 9/1993 |
| WO | WO-96/10954 | 4/1996 |
| WO | WO-96/24316 | 8/1996 |
| WO | WO-97/13450 | 4/1997 |
| WO | WO-99/05973 | 2/1999 |
| WO | WO-99/35974 | 7/1999 |
| WO | WO-00/10466 | 3/2000 |
| WO | WO-00/32111 | 6/2000 |
| WO | WO-01/39693 | 6/2001 |
| WO | WO-01/85035 | 11/2001 |
| WO | WO-2005/079674 | 6/2005 |
| WO | WO-2005/112852 | 12/2005 |

OTHER PUBLICATIONS

U.S. Appl. No. 11/223,324, Office Action dated Feb. 2, 2010.
Brazilian Application No. PI0215804-3, Office Action mailed on Aug. 25, 2010, 6 pages.
Goodrich, Jr. M.D., E. O. "An Anchor Technique for Stay Sutures", *Surgery*, vol. 64, No. 2 (Aug. 1968), pp. 416-417.
Abstract, Pavletic, "Use of an External SKin-Stretching Device for Wound Closure in Dogs adn Cats", *J. AM Vet. Med. Assoc.* 217 (3) Aug. 1, 2000, 350-354.
Abstract, Ritzman, T. K. "Use of an External Skin Stretching Device in a Guinea Pig", *Exotic DVM* Jan. 2001, 3(1), 31-35.
International Search Report and Written Opinion for PCT/US2006/018544, mailed on Dec. 11, 2006.
European Search Report, European Patent Application No. 12150140, mailed Mar. 26, 2012.

\* cited by examiner

TENSION TABLE

| ELASTOMER SIZE AND TYPE | DISTANCE STRETCHED | FORCE |
|---|---|---|
| | | |

FIG 18

SYSTEM AND METHOD FOR MOVING AND STRETCHING PLASTIC TISSUE

RELATED APPLICATION DATA

This application is a divisional of U.S. patent application Ser. No. 10/275,760, filed on Nov. 7, 2002, which issued as U.S. Pat. No. 7,429,265, which is a national phase of PCT/IB01/00796 filed May 9, 2001, which claims the benefit of U.S. Provisional Application No. 60/202,739, filed May 10, 2000, and U.S. Provisional Application No. 60/249,766, filed Nov. 17, 2000, the contents of all of which are incorporated herein in their entirety.

FIELD OF THE INVENTION

This invention relates generally to the moving and stretching of human and animal plastic tissue and more specifically to a system and method of moving and stretching plastic tissue using dynamic force.

BACKGROUND OF THE INVENTION

Elastic tissue returns to a minimum elastic, or relaxed, state when released from tension. In this relaxed state, tissue cells have a spherical shape, cell walls are thick and strong, and cell surface tensions are minimized and balanced. A cell in this minimum elastic state will remain relaxed, demonstrating behavior similar to a non-elastic material. The force required to elongate a cell in this state often approaches a force that will rupture or sheer intercellular bonds, causing localized failures or tears. Soft tissue in this minimum elastic state provides minimum surface coverage and has the highest reluctance to stretch. It is believed that a gentle but constant force below the sheer force threshold applied to tissue in combination with adequate hydration will, over time, restore the skin to the original elastic state. Additionally, this force can be applied to stretch tissue past the point of equilibrium (normal elastic range) to the maximum elastic range and create the thinnest possible configuration, covering the maximum surface area. If intercellular pressures in the tissue do not exceed the point at which intercellular bonds are compromised, the tissue remains at the maximum elastic state as healthy tissue, and normal biological processes will build additional cells to restore normal skin thickness and tension, which is described below as biological creep.

Plastic tissues, such as skin and muscle, possess certain viscous and elastic theological properties, and are therefore viscoelastic. Certain plastic tissues are able to increase surface area over time, which is described as "creep." Mechanical creep is the elongation of skin with a constant load over time, while biological creep refers to the generation of new tissue due to a chronic stretching force. A constant and unrelenting force applied a body tissue, such as skin or muscle, may result in both mechanical and biological creep. Mechanical creep restores the tension originally present but lost in the skin across the incision or wound by retensioning skin or soft tissue cells, thereby increasing skin coverage. Biological creep occurs more slowly and involves the creation of new tissue. Tissue expansion has long been part of the art of plastic surgery, traditionally accomplished with balloon-type tissue expanders embedded under the skin and externally inflated and increased over time to create expanded pockets of skin for procedures such as breast reconstruction after radical mastectomies, and stretching healthy tissue prior to plastic surgery for the creation of flaps for soft tissue closure.

Wound management, including treatment and care of large skin defects and severely retracted incisions, is an area of increasing importance in medicine today. There are many types of wounds and conditions that require treatment, including, but not limited to: diabetic ulcers and other chronic ulcers; venous stastis ulcers; pressure sores or ulcers; burns; post traumatic lesions, such as post disarticulation, post debridement, cutaneous gangrene, post colectomy, crush wounds with ischemic necrosis; collagen disease, including rheumatoid arthritis; vasculitis (lesions and ulcers caused by arterial insufficiency); amputation; fasciotomy; abdominal surgery; post sternotomy; necrotising fasciitis; trauma; wounds having exposed plates or bones; scar revision; skin lesions; bariatric surgery; blunt abdominal trauma with perforations; pancreatitis; neuropathic ulcers; compartment syndrome; and other subacute or chronic wounds. Treatment and care of these defects is challenging due to difficulties in closure of open wounds.

Compartment syndrome is a condition in which increased pressure in a limited space compromises the circulation and survival of the tissues within that space. Elevation of interstitial pressure in a closed facial compartment results in microvascular compromise within the compartment and vascular insufficiency, reducing blood flow. Capsulated internal pressure is created when swelling exceeds the elastomeric capacity of the skin. This condition is commonly caused by capillary infusion following, for example, trauma, inflammation, burns or intense muscle use. As duration and magnitude of interstitial pressure increase, necrosis of soft tissues eventually develops. If left untreated, it can lead to permanent injury to muscle, nerve and vascular structures, resulting in major loss of function, limb, and even life. These types of permanent injuries resulted in amputations prior to the development of aggressive treatments.

Objectives of treatment of compartment syndrome include minimizing deficits in function by promptly restoring local blood flow. This can be accomplished through surgical decompression, which consists of pressure release by an expedient fasciotomy in which each potentially limiting envelope, including skin, is opened over the entire length of the compartment. Expedient fasciotomy provides room for tissue expansion, which results in an instant relief in pressure, restores normal vascular function, and minimizes tissue death that would result from restricted circulation. The skin is left open after surgical decompression to prevent it from becoming a limiting envelope during the anticipated period of post-ischemic swelling. This large, open incision allows the engorged tissues to expand beyond normal dermal restriction and resume normal pressures. Over time, fluid is reabsorbed and tissues return to a pre-trauma size. In many cases, skin closure may be attempted three to five days after surgical decompression by direct suture or meshed skin graft. However, the elastomeric properties of the skin cause wound edge retraction over time, and make closure difficult or impossible. Objectives for closure of other wounds and skin defects are similar to those for closing a fasciotomy.

Two common methods of closure of wounds and skin defects include split thickness skin grafting and gradual closure. A split thickness skin graft involves removing a partial layer of skin from a donor site, usually an upper leg or thigh, and leaving the dermis at the donor site to re-epithelialize. In this manner, a viable skin repair patch can be transferred or grafted to cover a wound area. The graft is often meshed, (which involves cutting the skin in a series of rows of offset longitudinal interdigitating cuts) allowing the graft to stretch to cover two or three times greater an area as well as provide wound drainage while healing. Normal biological function of the skin heals the holes after the graft has been accepted. A meshed graft of this type requires a smaller donor area than a conventional non-meshed or full thickness skin graft. However, these methods do not provide optimal cosmesis or quality of skin cover. Other disadvantages of this method include pain at the donor site, creation of an additional disfiguring wound, and complications associated with incomplete "take" of the graft. In addition, skin grafting often requires immobilization of the limb, which increases the likelihood of contractures. The additional operation and prolongation of hospital stay is an additional economic burden.

Gradual, or progressive, closure is a second method of closure. This technique may involve suturing vessel loops to the wound edge and drawing them together with large sutures in a fashion similar to lacing a shoe. In addition, the wound edges may be progressively approximated with suture or sterile paper tape. The advantages of this gradual, or progressive, technique are numerous: no donor site is required for harvest of a graft, limb mobility is maintained, and superior cosmetic result, more durable skin coverage, better protection from full skin thickness and the maintenance of normal skin sensation may all be achieved.

Existing devices for effecting a gradual closure have many disadvantages. Current methods and devices draw wound edges together using mechanical devices such as screw-actuated devices that require repeated periodic adjustment because a relatively small skin movement substantially eliminates much of the closure force. Widely used existing closure techniques involve use of relatively inelastic materials, such as sutures or surgical tape. Excessive tension may cut the skin or cause necrosis due to point loading of the tissue. Current solutions include suture bolsters, suture bridges, use of staples as anchors at the wound edge, and the use of ligature wire to distribute the load along the wound margins. These approaches all rely on static ribbon or suture material, which must repeatedly be readjusted in order to function effectively, and even with this constant readjustment, maintenance of near constant tension over time is difficult, if not impossible, to achieve. Widely used traditional gradual closure methods rely on static force through fixed distance reduction, and do not provide continuous or dynamic tension.

Many current methods of open wound reduction employ static or non-yielding devices such as sutures or hard approximators, which reduce the distance between the wound margins and rely on the skin's natural elasticity to compensate for movement. One problem with these devices has been that when they are at the point of being most effective, when the skin is at the point of maximum stretch, additional skin tension created through motion, such as breathing or walking, creates stress points where the mechanical fasteners meet the wound margins, causing tearing and wound edge necrosis. This has generally required patients to remain immobile during the course of treatment. Existing systems for treating animals need not consider cosmetic result to such a degree as the healthy patient typically masks the wound site with fur, but cosmesis is a critical criteria in the measurement of a successful result from the system in the human application.

One existing device for effecting closure of a wound utilizes a constant tension, low-grade force to draw wound edges together. This device, the Proxiderm™ system, includes a pair of hooks carried by a pair of sliders that move along a path pulled by a pair of springs. This spring device is enclosed in a plastic housing and is available in four models with different curvature. The sharp hooks used in this system may damage the skin. The constant force used is a dictated force that is not variable.

Other closure devices are described in U.S. Pat. Nos. 5,234,462 and 5,649,960 to Pavletic, which disclose the use of elastomeric material to approximate wound margins, including rubber bands and other types of compressive and non-compressive materials. A kit disclosed by Pavletic requires bonding to the skin with an adhesive and also requires periodic adjustment to tighten the straps. One embodiment uses hooks and elastic loops, which must be replaced with smaller elastic loops to maintain tension. Another Pavletic embodiment uses a motor power source to provide a tightening means. The Pavletic patents do not disclose a system that eliminates the need to adjust the tension repeatedly, or a system that is self-regulating and self-adjusting.

One currently used device is the Sure-Closure device, which consists of two surgical needles, two U-shaped lexan polycarbonate arms with hooks on the bottom surface, a threaded tension bar and a polycarbonate ruler. The needles are threaded along the wound margin, and each arm is positioned above a needle, with the hooks piercing the skin and engaging the needles. The tension bar is then locked, and tension can be adjusted using the screw.

Existing methods of gradual wound closure fail to provide an effective gradual closure that restores original skin tensions lost across the wound. For example, the Proxiderm™ system has a single tension of 460 grams. In many instances, such as with the elderly or with compromised skin, this force is too great, resulting in localized failures, tears and necrosis. Many current devices are cumbersome, restrict patient mobility, must be completely removed for wound dressing and cleaning, and are usable in a relatively limited number of situations because of size constraints. Many also require a surgeon for reinstallation after removal for wound dressing. Finally, current devices cannot readily be used for radial closure of wounds due to their limited ability to pull in a single direction along an overhead beam, thereby restricting their application to parallel pulls along the same axis.

There is a need for a system providing for manipulation and control of tissue tensions on a living person or animal, utilizing both stretch and creep to restore and move plastic tissues. What is needed is a method and device for moving and stretching plastic tissue that is simple, easy to use, relatively inexpensive, extremely versatile, self-adjusting and capable of exerting relatively constant tension over a certain distance and at various intersecting angles in complex geometrical wounds.

SUMMARY OF THE INVENTION

Methods, systems and devices of this invention move and stretch any plastic tissue. For example, this invention is useful in the dynamic closure of large or small dermal wounds, incisions, or defects that may be associated with a variety of conditions, as well as in the stretching of healthy skin in preparation for a skin graft or other procedure. This invention involves the use of an elastomeric driver that may be formed in rods, bands, loops, sheets, nets, wires, or tubes, or other structures that can be stretched and exhibit relatively uniform retraction force over a relatively substantial distance, and anchors for attaching the elastomer to the plastic tissue. In the most simple use, such as closure of fasciotomies, the invention can be used to restore retracted skin to its original position.

This invention may also be used to stretch skin to cover an area where some of the original skin has been lost, such as might be the case with a localized burn, ulcer, or contracture or to stretch skin prior to a skin graft, flap, or other plastic surgical procedure. Depending on age, general health, skin condition, degree of skin hydration, and other factors, most skin can be stretched about 20%. Under ideal conditions, skin can be stretched as much as 60% over a period of weeks. In rare circumstances, stretching as much as 100% is possible. The viscoelastic properties of skin are discussed in Wilhelmi, et al., *Creep v. Stretch: A Review of the Viscoelastic Properties of Skin,* 215 Annals of Plastic Surgery 41 (August 1998), which is incorporated by reference herein.

This invention provides advances over current methods for moving and stretching plastic tissue through the introduction of gradual but unrelenting tension that is adjustable. A system according to this invention is virtually infinitely variable in stretching or closure force and can also be used in restricted areas where other skin closure systems would not fit, including under breasts, at the juncture of the neck and shoulder, and other such areas, and can be scaled up or down as required, using small anchors for ulcer closure and large anchors for abdominal closure. The elastomeric material may vary in thickness and cross section to achieve a near infinite range of tension as required.

This invention displays several critical advantages over the existing systems. Human skin varies dramatically in elasticity and thickness depending on age and health. Non-healthy patients, such as oncology patients, often present with compounding maladies such as thin, friable and ischemic skin at retracted wounds from procedures, such as a mastectomy, where a retracted incision is further irritated by radiation, which significantly weakens the skin. According to one embodiment of this invention, a variety of skin fixative components match the skin bonding strength to the required moving and stretching force to minimize necrosis and scarring. Additionally, various elastomers may be used in a multitude of ways to create a broad range of moving and stretching forces that match the counter-tractive tensions on multiple planes present in various locations. Unlike prior devices, such as the Proxiderm™ device, an overhead beam is not required, and therefore this invention is capable of providing both linear force and radial force exerted on multiple points.

According to one embodiment of this invention, dynamic force is used for moving and stretching plastic tissue, providing and maintaining a maximum safe traction pressure or force across a wound margin. The pressure remains below a pressure level that would create localized failure at the wound edge. In this manner, controlled constant and unrelenting tension is created, achieving maximum mechanical and biological yields to move and stretch plastic tissue, including closure of large retracted skin defects.

Dynamic force is used to draw wound edges together over time, using controlled and relentless counter-traction force. In one embodiment, this dynamic force is created using elastomers that are laced across a wound, allowing rapid removal for dressing changes and uninterrupted visualization of the wound bed during routine cleaning procedures. When tension adjustment is required, it can be accomplished quickly, and the elastomers can include an easily read indicator. Thus, the nursing staff may replace wound dressings and readily reapply the force specified by the surgeon. Utilizing dynamic force to move and stretch tissue offers the advantage of a relentless countertraction force, while allowing for expansion and contraction of the wound site, which greatly enhances patient mobility and is compliant with respiratory movements. In addition, an increased range of traction beyond the elasticity of the skin itself is provided. For example, a range of closure rates of 1.25 to 1.75 cm per day may be averaged over the course of treatment, which is considerably faster (about twice as fast) as the rates achieved using static counter traction methods of the prior art.

This invention accelerates the reduction in swelling by providing controlled radial pressure, which promotes migration of the edema fluid across the cell wall, enabling faster absorption by the lymphatic system. Thus, when applied to a fasciotomy, devices according to this invention accelerate the reduction in swelling. Traditional fasciotomy procedures provide release of intracompartmental pressure, but provide such release in an irreversible procedure. Methods and devices according to this invention provide controlled pressure release, when applied at the time of fasciotomy, allowing a controlled reabsorption of pressure within the swollen tissue at a level below the threshold that compromises circulation. Retraction of the skin is controlled which reduces the amount of reapproximation required to close the wound after swelling is reduced and compartment pressures are normalized.

BRIEF DESCRIPTION OF THE DRAWINGS

FIG. 18 is an example of a tension application table used with one embodiment of this invention.

DETAILED DESCRIPTION

Methods, systems and devices according to this invention provide a collection of components and techniques for moving and stretching plastic tissue. More specifically, the components are anchors and force applying components specifically including elastomeric components typically connected between and among two or more anchors. Methods, systems and devices according to this invention use dynamic opposing force that is equal to or greater than the elastomeric traction forces of the plastic tissue.

One system according to this invention includes at least one tissue anchor, which is an element that grips tissue using, for example, sutures, staples, flukes or prongs, adhesives, including surgical glue, or other suitable methods, and at least one elastomeric component. In one embodiment, the anchor is a staple. In a typical embodiment, multiple anchors are attached to the tissue proximate the edges of an open wound. Elastomeric components engage the anchors, providing a force that moves and stretches the tissue. In addition to anchors and elastomers, the system may include a measuring insertion tool and surgical staples. The system can be applied to a patient either during or anytime after a fasciotomy procedure or at any time moving or stretching tissue is required or desired.

Figure 1:
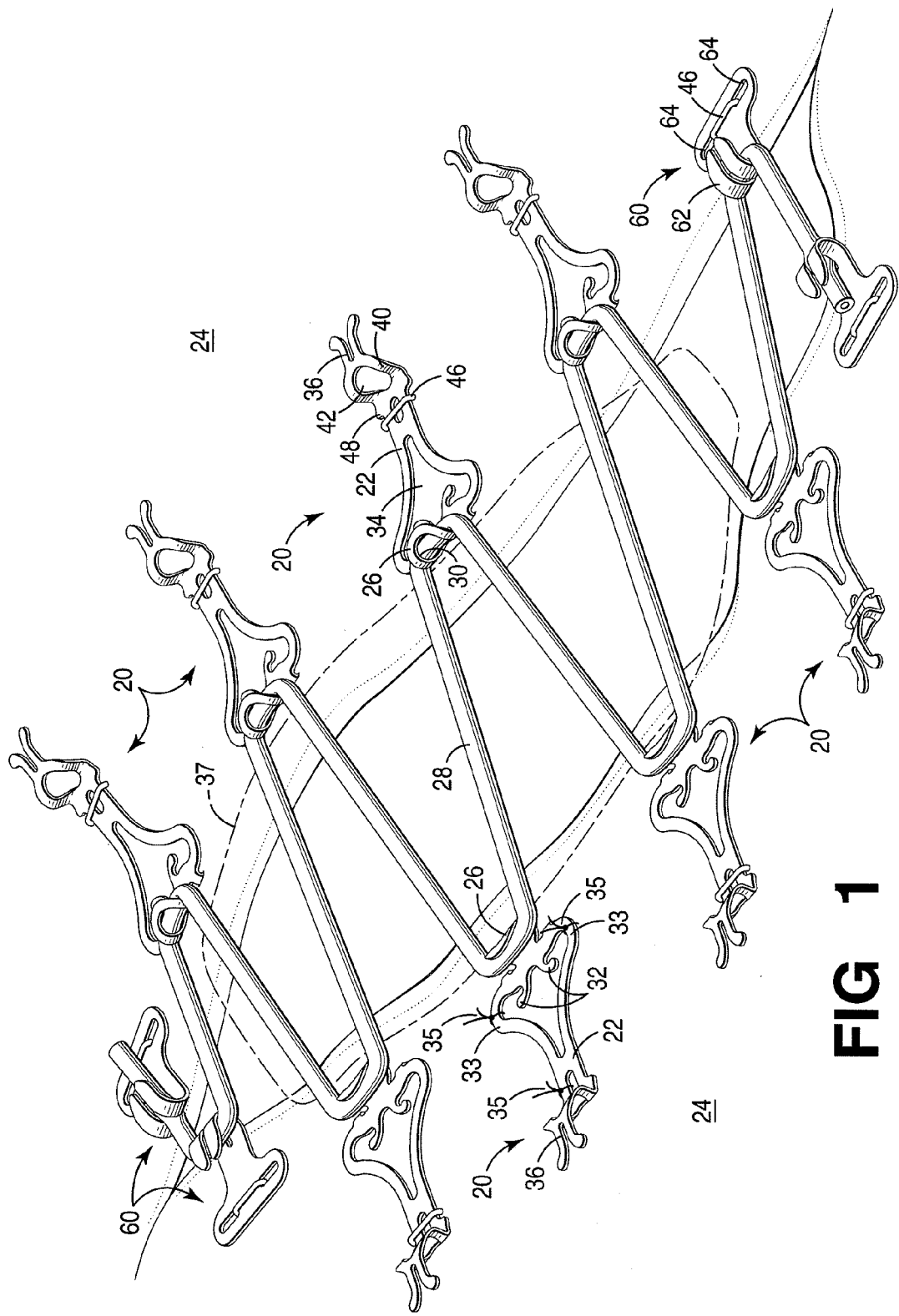
FIG. 1 is a perspective view of the system according to one embodiment of this invention.
Figure 2:
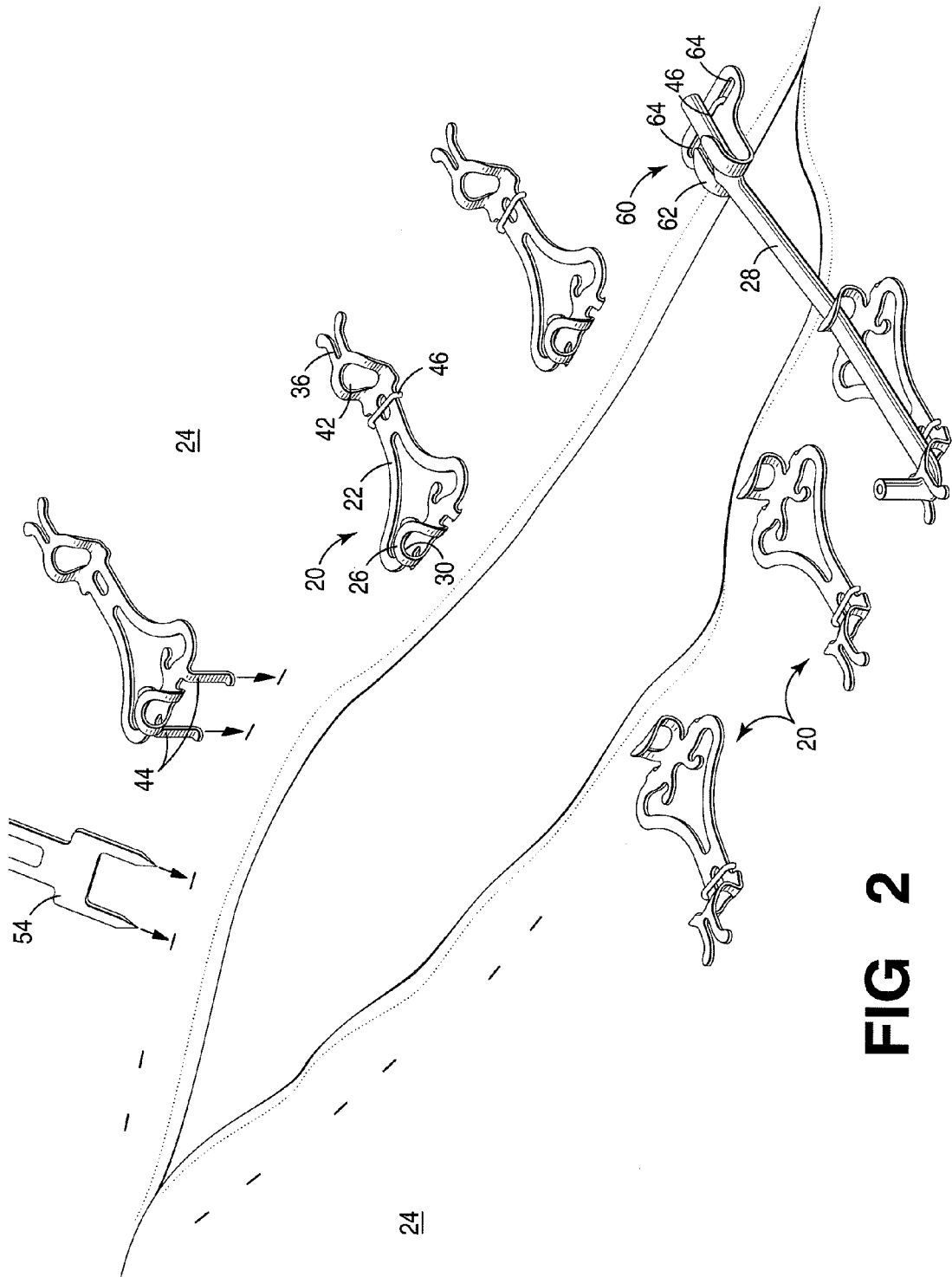
FIG. 2 a perspective view of the system depicted in FIG. 1 during the process of anchor attachment.
Figure 3:
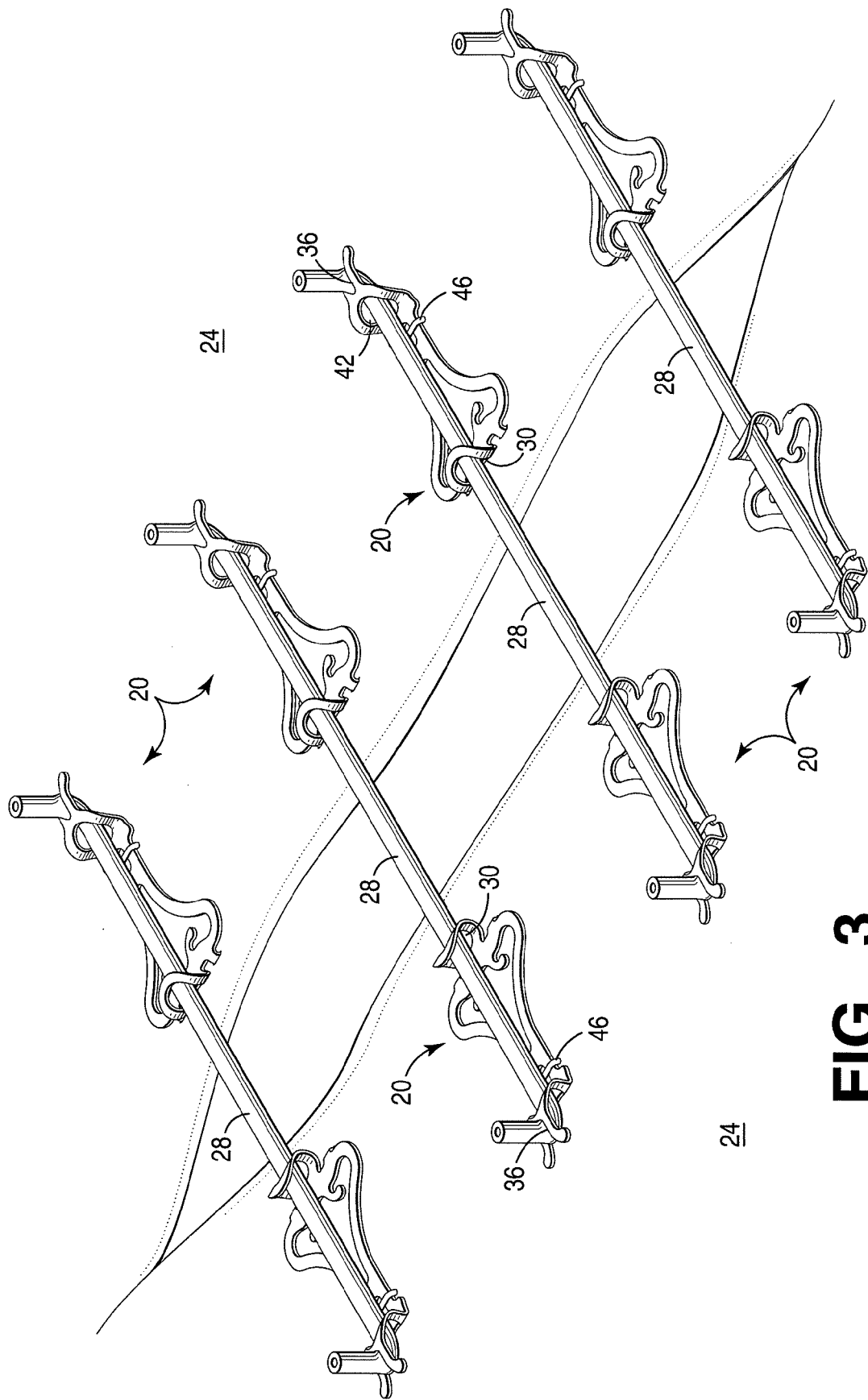
FIG. 3 is a perspective view of the system according to another embodiment of this invention.
Figure 4:
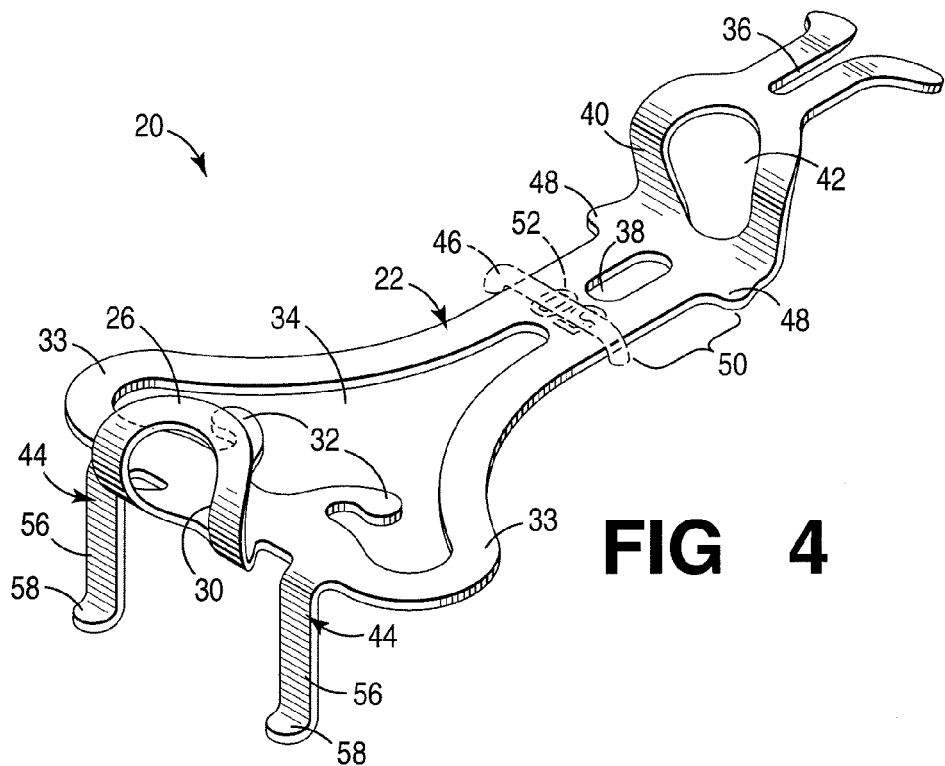
FIG. 4 is an enlarged view of an anchor of the system of FIGS. 1-3.
Figure 5:
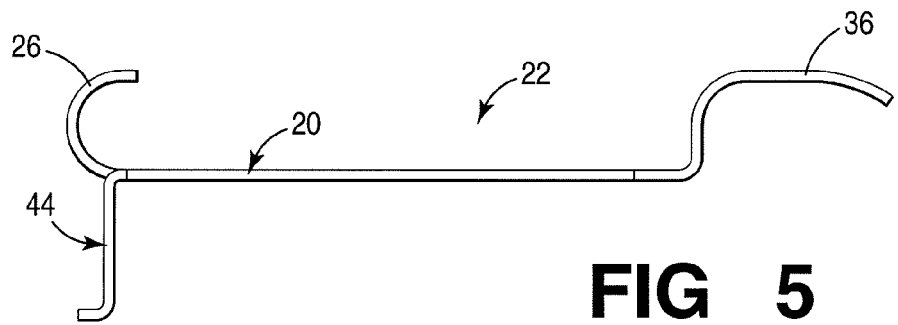
FIG. 5 is a side view of the anchor shown in FIG. 4.
Figure 6:
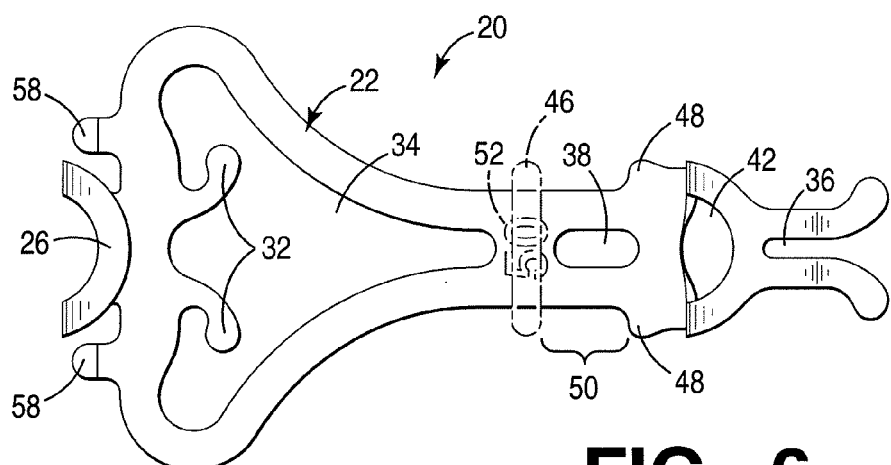
FIG. 6 is a top plan view of the anchor shown in FIG. 4.

FIGS. 1-3 illustrate a wound closure system according to one embodiment of this invention. A fluke-bearing tissue anchor 20, shown in detail in FIGS. 4-6, has a generally flat body 22 that lies against skin 24, and a hook 26 around which elastomer 28, shown in FIGS. 1-3, may be positioned. Hook 26 of fluke-bearing anchor 20 is perforated by forward eye 30, through which elastomer 28 may optionally pass. Ears 32 extend from hips 33 into opening 34, forward of jam cleat 36 and slot 38. Ears 32 form a staple landing for further stabilization of the forward portion of the anchor, if required.

Figure 7:
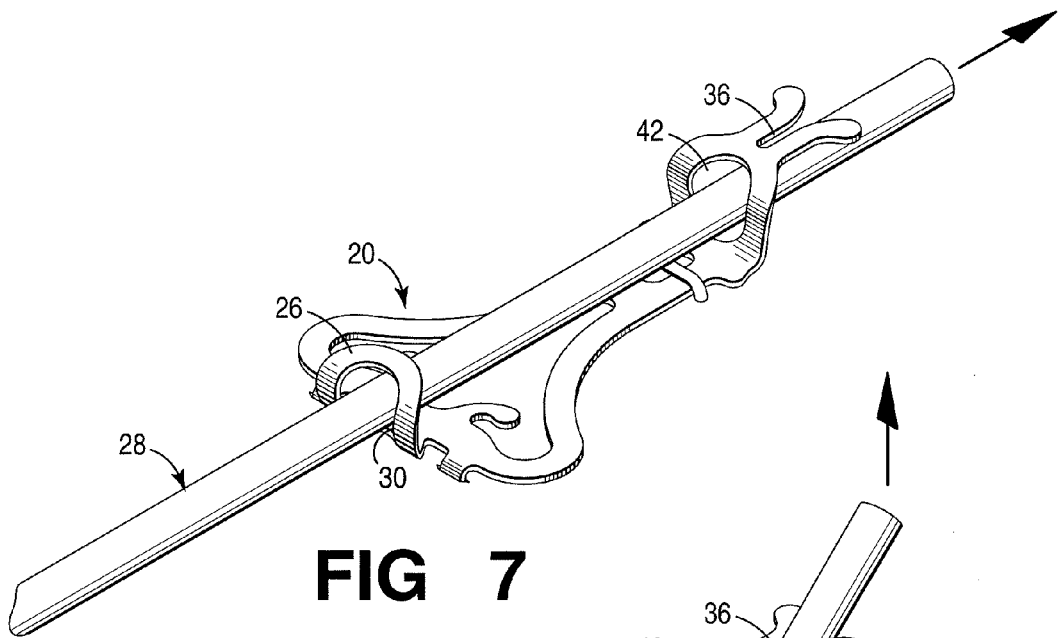
FIG. 7-9 illustrate an anchor and elastomer of this invention at successive stages during the process of elastomer attachment.
Figure 8:
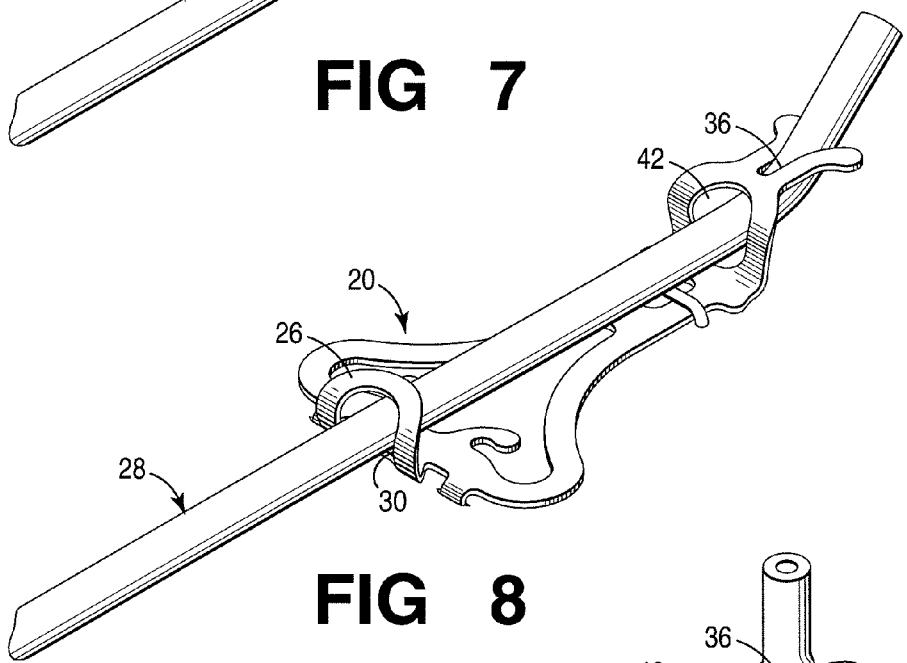
Figure 9:
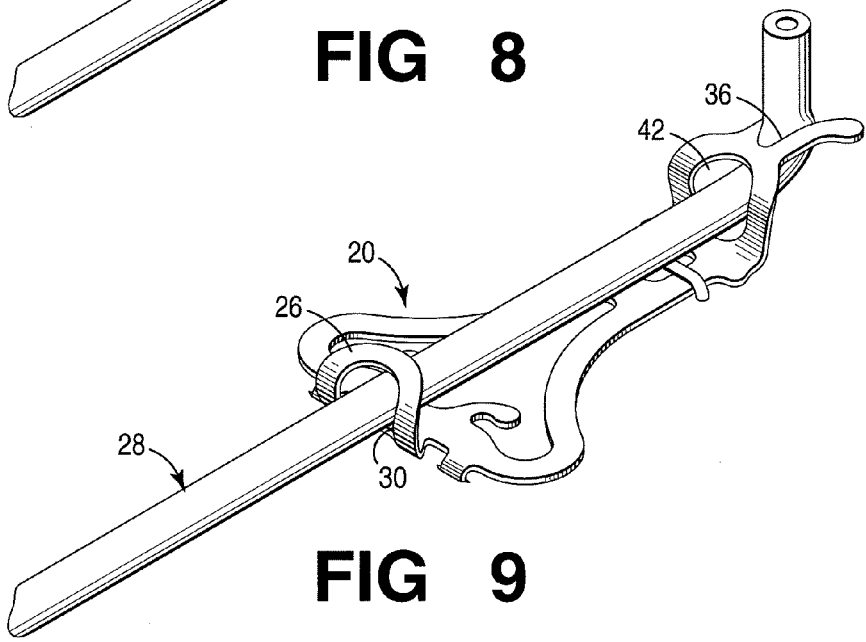

Elastomer 28 may be retained by jam cleat 36, as illustrated in FIGS. 7-9. Frame 40 surrounds window 42, through which elastomer 28 may optionally pass. Elastomer 28 may engage jam cleat 36 either from eye 30 or from a subcutaneous presentation through the center opening 34 of anchor 20. Jam cleat 36 may engage elastomer 28 when tensioned and lock elastomer 28 in place when an end of elastomer 28 is relaxed. Jam cleat 36 can also allow elastomer 28 to slip when the load applied exceeds a safe working tension by a margin that is determined by the size of the cleat, the elastomer size, and elastomeric material durometer. Frame 40 can provide a second fail safe release by sizing it to deform through bending when a designated force is applied in excess of the working load limit of jam cleat 36. Deformation of frame 40 causes jam cleat 36 to tilt toward the direction of pull and release elastomer 28, providing release at a safe working load and providing a substantial safe working margin prior to the occurrence of any traumatic failure at flukes 44.

Fluke-bearing tissue anchor 20 provides a relatively wide area of contact with skin 24, allowing maximum levels of counter-traction to be applied while minimizing localized tissue failures. Fluke-bearing tissue anchor 20 may be attached to skin 24 with at least one staple 46, or by sutures 35 which may pass at least partially through and on one or both sides of slot 38 and around one or both of hips 33 or by surgical skin glue, or other adhesive. Staples may be installed using a surgical stapler, while slot 38 provides access to staple 46 for ease of removal of staple 46. Adjacent to slot 38 is land 48, which stops movement of staple 46 at the rear end of staple travel way 50 that extends between land 48 and indicia 52. Indicia 52 may be a half thickness etch mark used both for part identification and as a visual target by the surgeon for locating the position of the rear staple. Indicia 52 may be chemically milled onto body 22 or may be applied in any other suitable manner. Travel way 50 provides staple 46 unrestricted travel, allowing for the skin contribution and differential stretch between flukes 44 and anchor body 22 that would occur in skin located directly under anchor body 22. Land 48 limits rearward migration of staple 46. Securing the anchor with a staple in this manner counteracts the tip-up force under high load at high stress traction points. Travel way 50 allows body 22 of anchor 20 to slide in a direction roughly perpendicular to the wound, but holds anchor 20 firmly against skin 24.

Marking instrument 54, shown in FIG. 2, is used to mark skin 24 prior to attachment of anchor 20. As shown in FIGS. 1 and 2, insertion of prongs or flukes 44 having legs 56 and feet 58 into and penetrating the dermal layers of skin 24 holds fluke-bearing tissue anchor 20 firmly in place. Thus, flukes 44 act as grapples, engaging skin 24 because of their shape and angle, and remaining engaged under tension. Feet 58 aid in this grappling function, preventing fluke-bearing anchor 20 from popping out of the skin, and serve as a safety feature, preventing flukes 44 from being driven further into the tissue if direct pressure is applied to anchor 20. Flukes 44 may be disengaged from skin 24 by releasing the tension exerted by elastomer 28 and withdrawing flukes 44 at an angle opposite to the angle of engagement.

Flukes 44, shown in the drawings, are merely illustrative, and the flukes may have other cross sectional and longitudinal shapes and could conceivably be bent in the process of installation. As an example, one variation of flukes 44 could have wider and longer legs and feet. Flukes 44 could be round rather than square or rectangular in cross section. In another embodiment, the anchor incorporates the staple function so that the anchor includes prongs that bend and capture the skin similar to the prongs on a staple. In this manner, the anchor functions as both an anchor and a staple.

Marking instrument 54 is designed to fit on a standard scalpel handle and provides a visual reference for the surgeon to puncture skin 24 for insertion of flukes 44 of fluke-bearing tissue anchor 20. Marking instrument 54 is used either with surgical ink or in such a fashion as to produce small depression marks in the skin, which act as guide marks to the surgeon to produce pairs of small puncture wounds with a No. 11 blade or other suitable blade or instrument. This allows flukes 44 of fluke-bearing tissue anchor 20 to be inserted through the dermal layers of skin 24.

In one embodiment of this invention, such as shown in FIGS. 1-6, each pair of skin anchors provides a controlled dynamic stretching or closure force between about 0 and about 1000 grams. In an alternate embodiment, components of this invention are scaled down and exert lesser force, while another embodiment includes components on a larger scale and therefore exert a greater force. Thus, fluke-bearing tissue anchor 20 and all of the anchor designs described herein may be produced in a variety of sizes. The anchors would typically have a body length of about 5 mm to about 60 mm and a body width of about 2 mm to about 50 mm. The smallest anchors for fine tissue closure would typically have a body width of about 2 mm to about 10 mm and a body length of about 5 mm to about 15 mm. Anchors for general surgical use would typically have a body width of about 10 mm to about 25 mm and a body length of about 20 mm to about 30 mm. In a large embodiment for treatment of abdominal defects, the anchors would typically have a body width of about 20 mm to about 50 mm and a body length of about 25 mm to about 60 mm.

Flukeless tissue anchor 60, also shown in FIGS. 1 and 2, has a split hook 62, which may act as either a hook around which elastomer 28 is positioned or a jam cleat within which elastomer 28 is captured. Flukeless anchor 60 has at least one slot 64 for receiving a staple or sutures. Alternatively or additionally, flukeless anchor 60 may be held in place with a surgical skin glue or other adhesive. Flukeless anchor 60 may be used when it is necessary to place an anchor near field, or in close proximity to the wound. The term "near field" refers to the area within 2 cm of the incision or wound edge, and is derived from the phrase "near the surgical field." Flukeless anchors 60 are most often used at the wound edge or at the end of the incision and often in opposing pairs. One advantage of flukeless anchor 60 is that puncture wounds for flukes are not required. Therefore, flukeless anchor 60 may also be used when a less invasive procedure is desired.

As an example, methods and devices according to this invention may be useful in one or more of moving and stretching facial plastic tissue. In one embodiment, flukeless anchors are provided in a smaller format and used for curing a facial defect. In this manner, facial defects may be treated in a less invasive manner since puncture marks are not required or are limited to those made by staples. In this embodiment, reduced size flukeless anchors may be attached to the skin using an adhesive, surgical glue, or other suitable method.

In one embodiment, flukeless tissue anchor 60 is used in conjunction with a viscoelastic suture, such as a suture made of material such as Silastic™ or latex. Generally, the viscoelastic suture is inserted outside of the wound margin and extends across the wound, exiting the skin outside the opposite wound margin. Flukeless tissue anchor 60 may be used to capture the suture as it exits the skin, linking the system to the suture. In this embodiment, flukeless tissue anchor 60 acts as a grommet, removing the point load from the suture exit hole to reduce the occurrence of localized failures, and also allows adjustment of the tension across the wound. Reducing localized failures also reduces scarring. This combination of a viscoelastic suture and an anchor creates a linear plane of pull, so that the skin is moved and stretched and the wound is reduced across the shortest possible distance, and it is unnecessary to follow the contour of a body cavity. This is important in situations such as in the case of severely emaciated patients with a retracted abdominal wound and in cases where a large cavity exists after removal of a tumor. In another embodiment, such a suture is used with at least one fluke-bearing tissue anchor. One example of a suitable suture is described in U.S. Pat. No. 5,895,413 to Nordstrom, the entirety of which is incorporated by reference herein.

In an alternate embodiment, this system is used with a through and through suture, which is a suture through all layers: skin, subcutis, fascia, muscle and peritoneum. In this embodiment, a through and through suture is secured to an anchor in order to distribute the load.

Elastomer 28, also shown in FIGS. 1-3, may be threaded through eye 30 of hook 26 of fluke-bearing tissue anchor 20, may pass around hook 26 of fluke-bearing tissue anchor 20 or around split hook 62 of flukeless anchor 60, or, may be gripped by jam cleat 36 or split hook 62. As illustrated in FIG. 1, elastomer 28 may be "laced" through a series of anchor hooks by passing around hooks of each anchor unit on the wound margin, or edge. Elastomer 28 may engage jam cleat 36 (passing first through window 42) or split hook 62 to terminate the lace end. As illustrated in FIG. 3, elastomers 28 may be used with sets of paired anchors. Opposite ends of elastomer 28 are threaded through eye 30 of hook 26 of fluke-bearing anchor 20, and then also through window 42 and jam cleat 36. This method allows for the control of unbalanced wound tension and is desirable where different closure forces or alternate pull solutions are required. Use of elastomers 28 with the anchors as described allows the device to act in a biaxial plane, providing treatment of wounds on curved body surfaces such as the feet.

Elastomer 28 may be made from virtually any elastomeric material acceptable for use near open wounds, including, but not limited to, latex or silicone rubber, natural rubber, GR-S, neoprene, nitrile-butyl-polysulfide, ethylene-polyurethane, polyurethane, or any other suitable material which exhibits the property of exerting a return force when held in an elongated state. Elastomer 28 provides a dynamic opposing force equal or greater than the natural occurring elastomeric traction forces of the skin. Elastomers of this invention may be formed in tubes with typical external dimensions of about 0.125 inch, however, alternative shapes, sizes and strengths may be appropriate in some situations. Elastomers of this invention are generally not endless loops but rather are lengths of a single strand, sometimes called a "monostrand," and may be either solid or hollow. In some instances, multiple strands or endless loops or bands may be used. Significantly, the elastomers used in practicing this invention may be secured to an anchor component at virtually any point along the elastomer, providing variable tension within the elastic limits of the elastomer.

Figure 10:
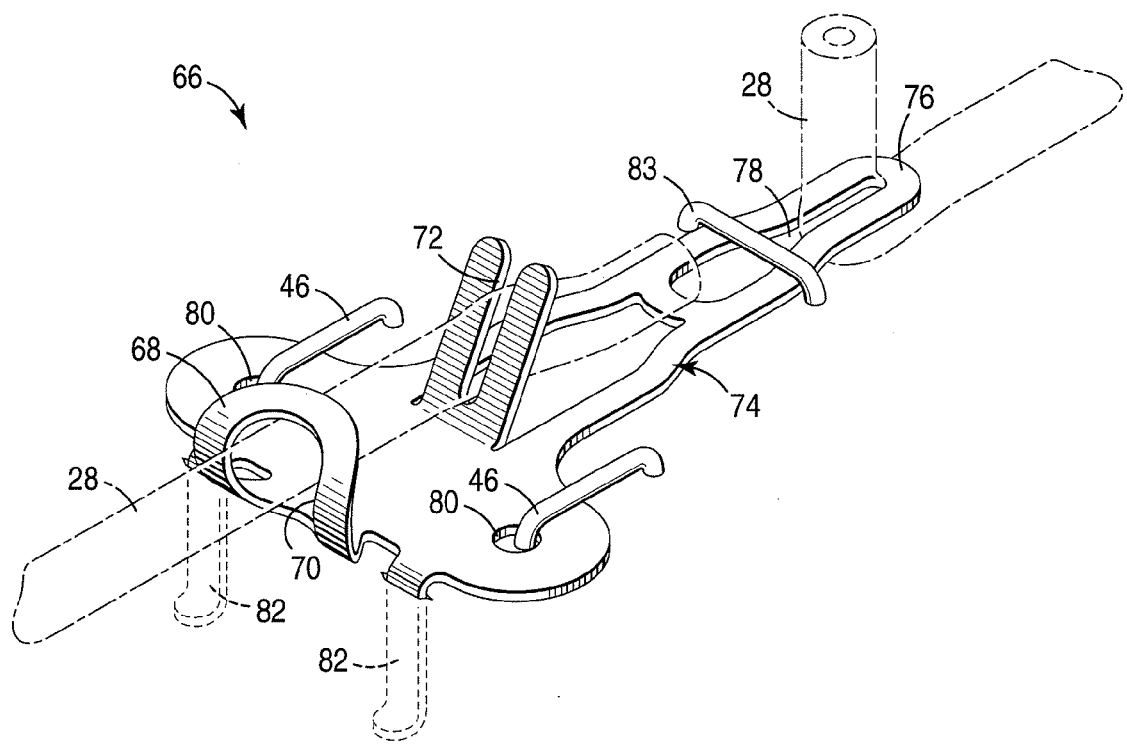
FIGS. 10-13 are perspective views of alternative embodiments of an anchor according to this invention.

FIG. 10 illustrates an alternative embodiment of a fluke-bearing tissue anchor. This alternative fluke-bearing tissue anchor 66 has hook 68, which is perforated by eye 70. Jam cleat 72 projects from body 74 and a stabilizing tail 76 projects from body 74 in the same plane and carries keyhole cleat 78. Body 74 also has staple apertures 80. FIG. 10 shows one end of elastomer 28 terminated using jam cleat 72 and positioned by eye 70 of hook 68. Another elastomer end is secured in keyhole cleat 78. Staples 46 are received in staple apertures 80 and assist flukes 82 in holding fluke-bearing anchor 66 in place. Ballast staple 83 is inserted across stabilizing tail 76 and counteracts the tip-up force under high load at high stress traction points. Ballast staple 83 allows stabilizing tail 76 to slide in a direction roughly perpendicular to the wound, but holds fluke-bearing anchor 66 firmly against the skin. Elastomer 28 is locked into keyhole cleat 78 of fluke-bearing anchor 66, allowing elastomer 28 to encircle an object or limb and allowing one end of elastomer 28 to be entrapped in jam cleat 72 and the second end of elastomer 28 to be trapped by keyhole cleat 78. In this manner, a single anchor and an elastomer may provide radial tension.

Figure 11:
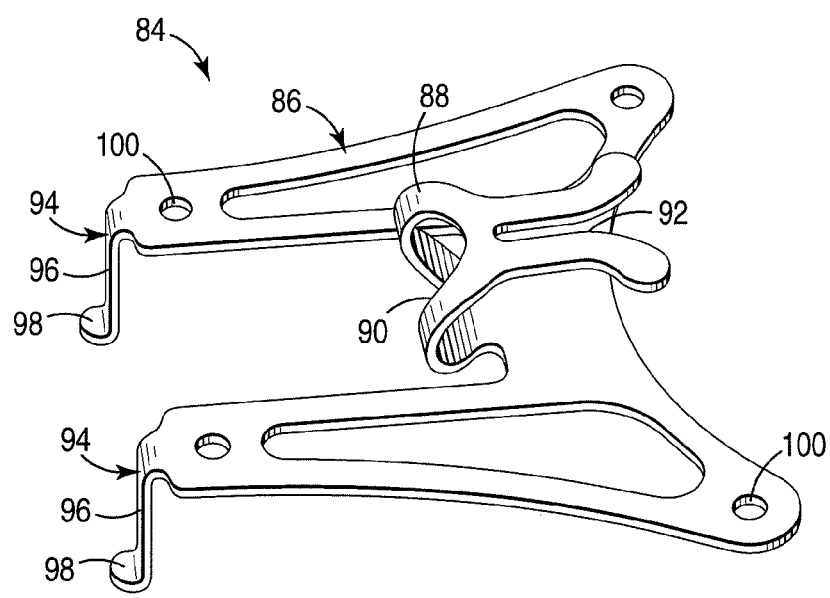

FIG. 11 illustrates another alternative embodiment of a fluke-bearing tissue anchor of this invention. Alternative fluke-bearing anchor 84 has a generally flat body 86 that lies against the skin. Hook 88 of alternate fluke-bearing tissue anchor 84 is perforated by eye 90 through which elastomer 28 may optionally pass, and is split by cleat 92, which may retain elastomer 28. Elastomer 28 may pass through eye 90 and be retained by cleat 92. Alternative fluke-bearing anchor 84 also has flukes 94, each of which include a leg 96 and a foot 98. Alternative fluke-bearing anchor 84 may be attached to the skin with at least one staple or by sutures passing through slots 100, or with surgical skin glue or other adhesive.

Figure 12:
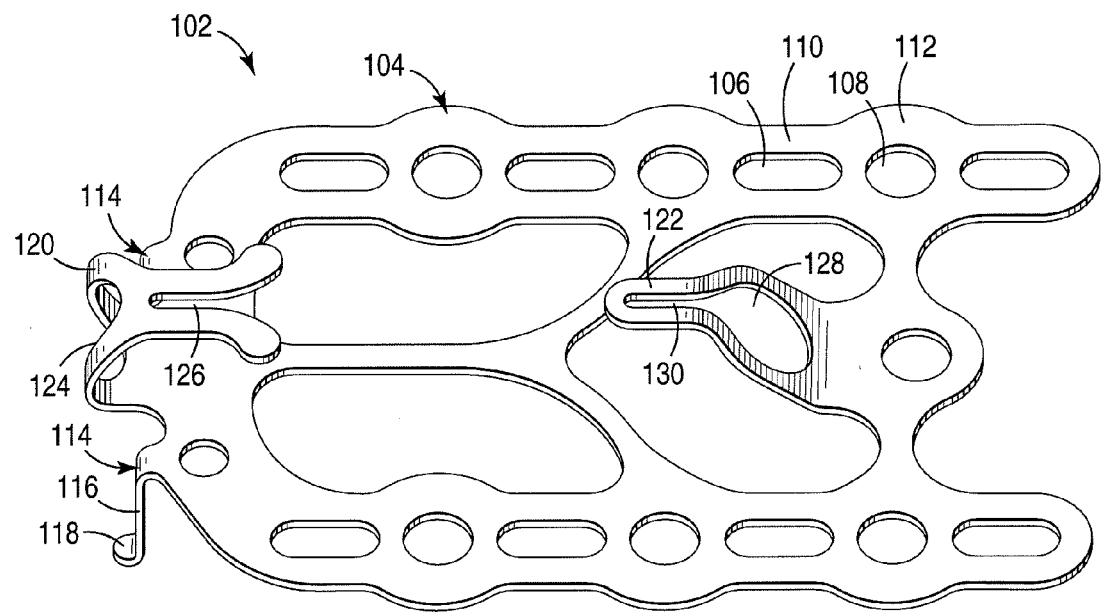

FIG. 12 illustrates yet another embodiment of an anchor of this invention. Tractor anchor 102 has a generally flat body 104, the edges of which are perforated by alternating slots 106 and holes 108. The spacing of slots 106 and holes 108 accommodates all standard skin staples. A staple may be placed through a slot and over narrow arm 110, and projections 112 prevent staples from sliding beyond narrow arm 110. Tractor anchor 102 has flukes 114, including legs 116 and feet 118.

Figure 13:
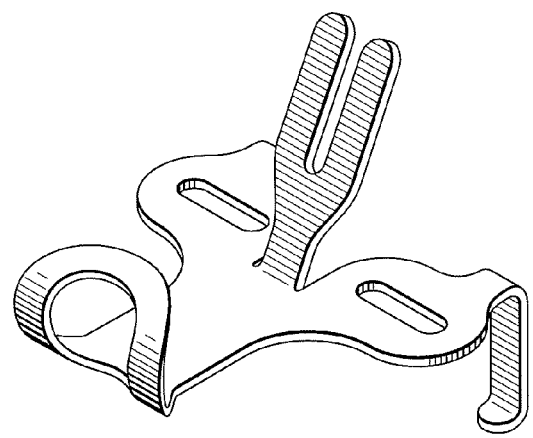

Tractor anchor 102 also has two cleats: front hook 120 and rear cleat projection 122. Front hook 120 is perforated by eye 124 through which elastomer 28 may optionally pass, and has cleat 126, which may retain elastomer 28. Rear cleat projection 122 is perforated by rear eye 128, through which elastomer 28 may optionally pass, and is split by cleat 130, which may retain elastomer 28. This double cleat design allows use of two rows of anchors on each wound margin since one or more elastomers may be attached at the front hook and rear cleat. In this embodiment, tractor anchor 102 is placed at the wound margin, while another anchor, including a tractor anchor or any of the anchors described herein, is placed at a greater distance from the wound, forming two rows of anchors. This alternative embodiment further dissipates load across the anchors. FIG. 13 illustrates yet another alternative embodiment of a fluke-bearing tissue anchor that includes a jam cleat and a hook perforated by an eye.

Anchor 20 and any of the other anchors described and illustrated herein may be fabricated from metal, plastic or other suitable materials. For instance, the anchors may be made by chemically etching 0.015 inch sheets of 304 stainless steel using a bookmatched two side photo resist chemical milling process to form appropriately-shaped anchor blanks that are then bent into their finished shape. This anchor is tab-less free etched and the logo and identifier marks are half etched in a single process. The photo resist mask is stripped and the anchor is tumbled in abrasive media for fine deburring before final cleaning and processing.

In one embodiment, the anchors are formed from plastic, or other suitable material. In another embodiment, the anchors are disposable. In yet another embodiment, disposable anchors are attached to the skin using a pressure sensitive adhesive with peel off backing that is attached to the bottom surface of the anchor component.

Figure 14:
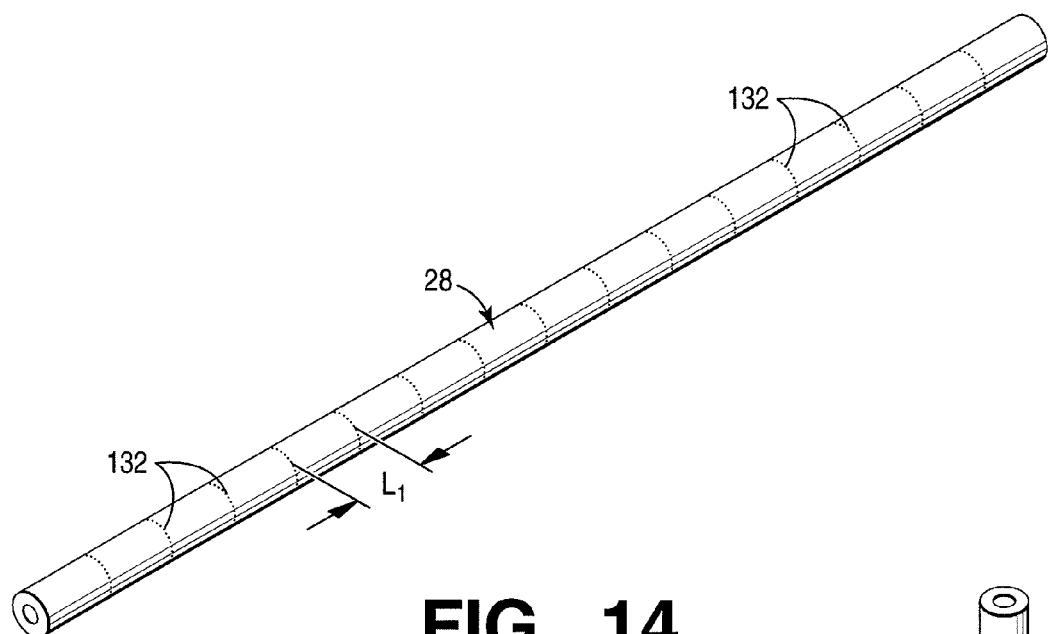
FIG. 14 is a perspective view of an unstretched elastomer according to this invention.
Figure 15:
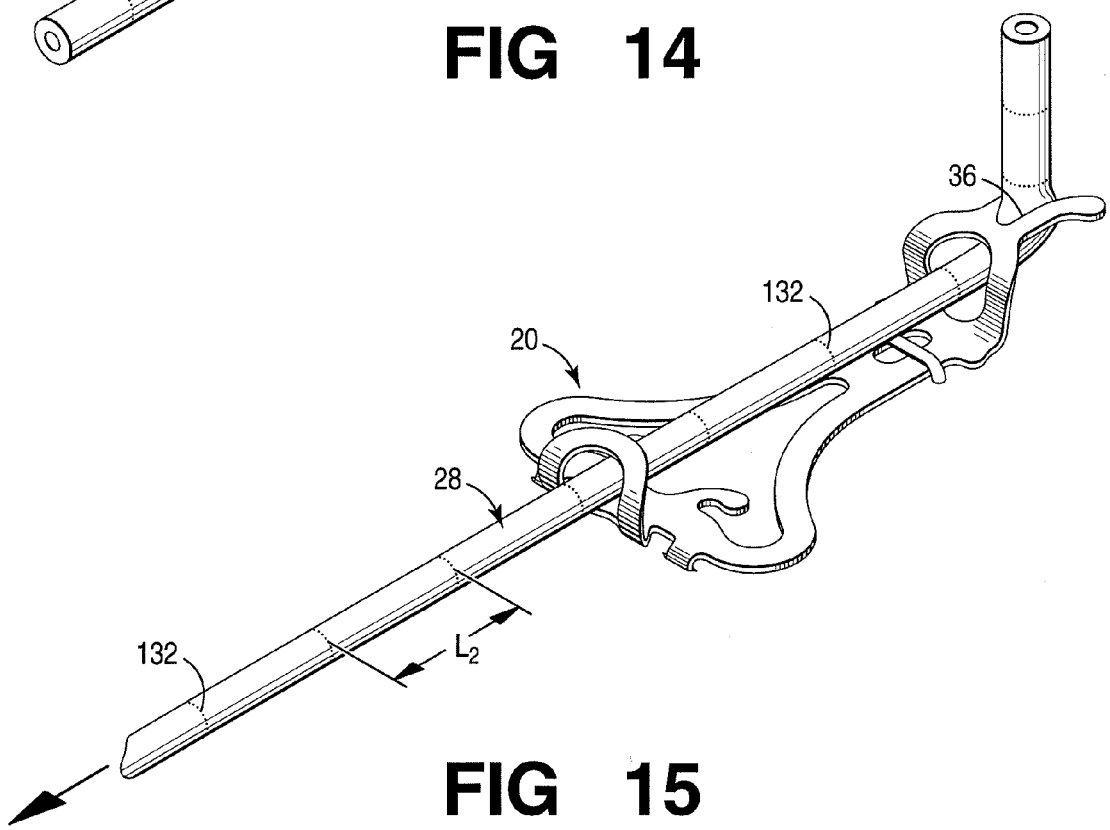
FIG. 15 is a perspective view of the elastomer of FIG. 14 attached to an anchor and stretched according to this invention.

FIGS. 14 and 15 illustrate an elastomer of this invention having an integral tension indication feature. Indicia 132 on elastomer 28 are used to indicate tension, and may be either marked (e.g. with colorant such as ink, paint, stain, dye or other colorant) onto the elastomer, or may be a raised ring, or annular depression, or any other suitable mechanism. In one embodiment, indicia 132 are spaced at a distance of one centimeter. Among other ways of placing indicia on elastomer 28, equally spaced indicia could be marked on elastomer 28 using a pen or other writing instrument by reference to a ruler or inserted through slots in an INCRA® marking rule or other device having spaced apertures. The indicia 132 are spaced at a distance L1 when the elastomer is in a resting state. When the elastomer is stretched, the distance between adjacent indicia 132 increases to L2. When the appropriate amount of tension to be applied is determined, the distance between the elastomers, L2, is measured and recorded so that it may be reproduced accurately after removal of the system for any reason, such as changing the dressings. Measurement of the difference in the distance, L1/L2, can enable the surgeon to determine how much tension is being applied by reference to a previous determination of the force exerted by a like elastomer (same type and size) stretched the same distance. Such information can be set forth in a table, as illustrated in FIG. 18, to which a surgeon can refer in order to convert a measured distance into an amount of tension.

Figure 16:
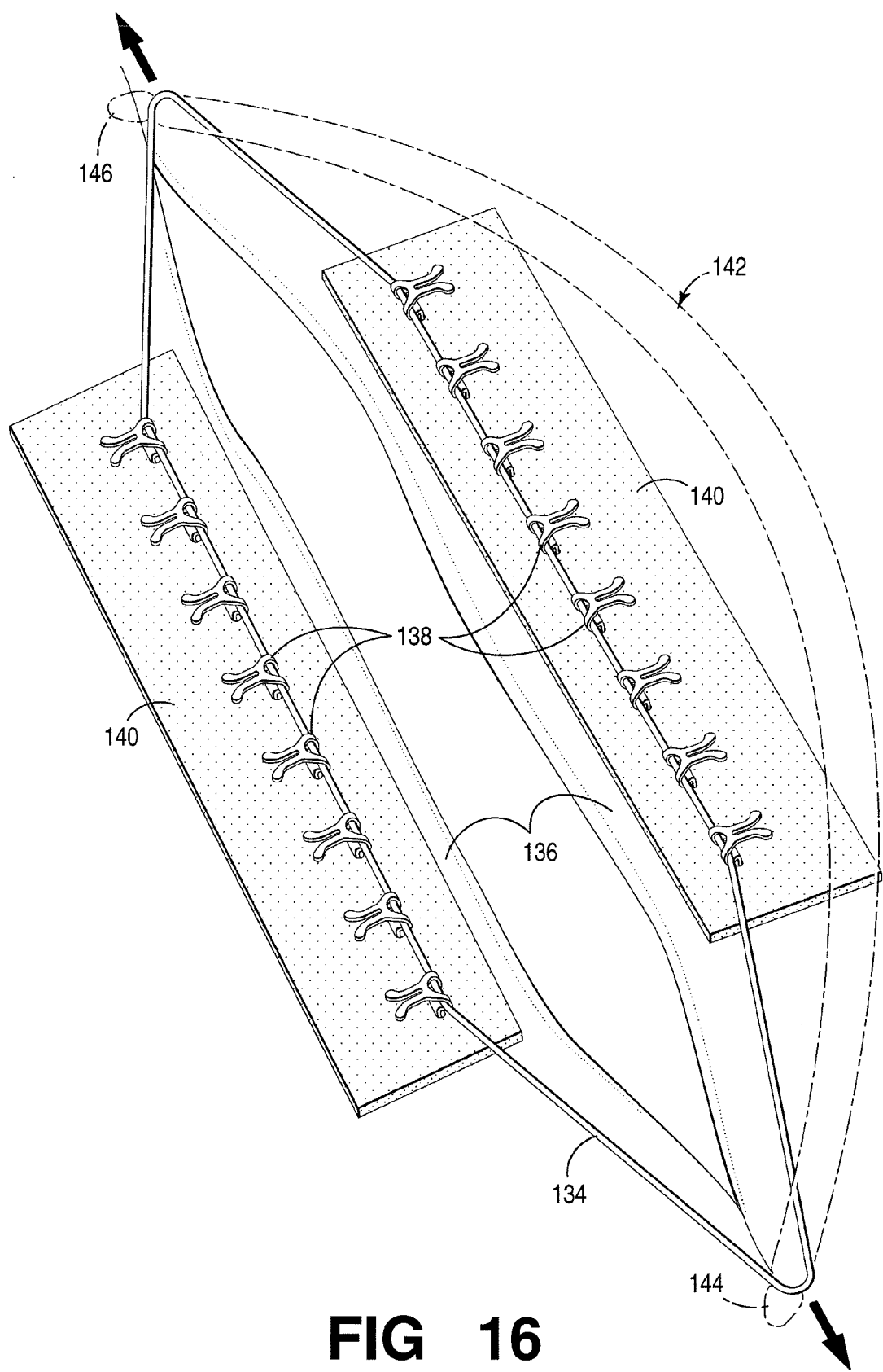
FIG. 16 is a perspective view of a wound closure system according to another alternative embodiment of this invention.

In yet another embodiment of this invention, illustrated in FIG. 16, a dynamic wound closing force is applied to a wound by attaching a loop of suture 134 to the wound margin 136 with small anchors or clips 138. Wound margins 136 are drawn together by applying force to suture 134, as shown in FIG. 16, along the length of the wound. This alternative is shown in FIG. 16 using medical tape 140, further described below, but may be accomplished using any of the anchor attachment methods described herein. Force is applied by engaging suture 134 with opposite ends of a bow 142, which may be wood, plastic, steel, or other suitable material that can be deformed into a bow shape but that seeks to straighten, thereby further separating the bow ends 144 and 146.

This invention may be applied in a clinical setting using local anesthetic. The surgeon evaluates which direction the skin needs to be contracted to facilitate closure. The wound length is measured in order to estimate the number of anchors required. The appropriate spacing of anchors will depend on the location and nature of the wound and other factors. A long wound on a human forearm might, for instance, use anchors that are placed about every three centimeters. A skin marker is used to draw a line about one centimeter from the margin, or edge, of the wound. Anchors are then installed, generally starting at the center of the wound, and typically in opposing pairs. The surgeon may choose a flukeless tissue anchor for use near the incision. A flukeless tissue anchor may be installed using a single surgical staple for light loads, or multiple staples or sutures for higher loads.

Alternatively, the surgeon may choose to install a fluke-bearing tissue anchor, which is generally used at a distance greater that two centimeters from the incision margin or edge and in circumstances where the traction will be applied beyond the anchor range of a flukeless tissue anchor, or one of the other anchors described above. A fluke-bearing tissue anchor may be used when it is desirable to avoid eversion of the wound edges, which may interfere with healing. Marking instrument 54 is used to provide guide marks to the surgeon for insertion of flukes 44 of fluke-bearing anchor 20 into skin 24 and stab wounds are made with a suitable blade, such as a #11 blade. Fluke-bearing tissue anchor 20 is then stapled, sutured or glued to secure it in place. If secured using at least one staple, a staple 46 is installed across travel way 50, allowing movement of anchor 20, thus preventing flukes 44 from digging into the sub-dermal layers of the skin, which can result from high counter-traction loads presenting off-axis thrust beyond the anti-torque forces provided by the dermis. A second staple may be installed across ears 32 if an increase in stabilization of the forward portion of fluke-bearing tissue anchor 20 is required.

The wound bed is dressed with a either a wet, dry, or other suitable dressing 37 (shown in FIG. 1). One such suitable dressing is Duoderm®, available from Smith & Nephew, or Tegaderm®, available from 3M. Elastomers 28 are applied, either in a lace fashion, as illustrated in FIG. 1, or by connecting two opposing anchors with one length of elastomer, as illustrated in FIG. 3. Additionally, the length of elastomer may wrap around the body part. Elastomers 28 apply a relatively constant force over a relatively large distance. The laced version of elastomers 28 is used when even amounts of tension are desired along a shear plane, such as is typically desired with a long, straight incision. A length of elastomer between two opposed anchors is used individually or in multiples when an irregularly shaped defect requires varied forces along more than one thrust plane. This would be typical of a Z-plasty, an L-flap incision or an incision not on the transdermal plane. A single elastomer 28 may also be used to encircle an object or wound and create radial tension. Elastomers 28 may be unlaced or uncleated repeatedly to allow for easy dressing changes, re-positioning, and re-tensioning.

In an embodiment of this invention used in the closure of a fasciotomy, this method of gradual wound closure eliminates the need for later suturing because this device approximates the edges of the wound, allowing the wound to heal as if sutures were in place. Elimination of delayed closure provides treatment in a single surgical intervention.

Figure 17:
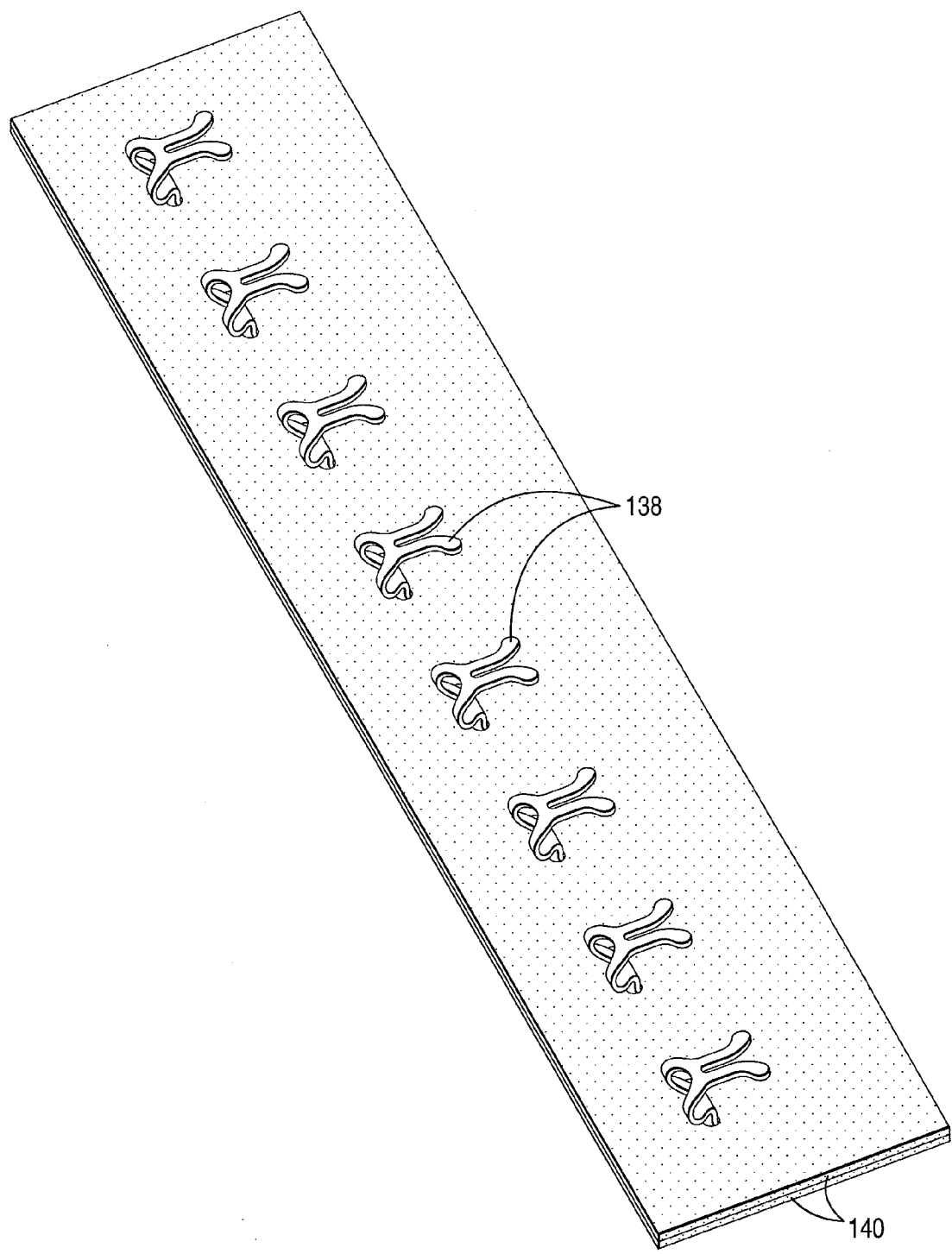
FIG. 17 is a perspective view of attachment of anchors according to yet another embodiment of this invention.

In an alternative embodiment of this invention, anchors, including any of the anchors described herein, are mounted on medical tape, such as pressure sensitive adhesive backed tape, as shown in FIG. 17. In this embodiment, the tape is attached to the patient at the wound margins. In another embodiment, the cleats are manufactured with an integral tape anchor feature to allow them to be sandwiched between two layers of medical tape. Such an integral tape anchor feature may be a structure having a large surface area with many through holes, such as a honeycomb grid, or a circle, or other suitable structure.

The system and methods of moving and stretching plastic tissue according to this invention are not confined to the embodiments described herein but include variations and modifications within the scope and spirit of the foregoing description and the accompanying drawings. For instance, the scale of the components of the invention can vary quite substantially depending on the nature and location of the tissue with which the invention is used. The configuration of the anchors can also be varied for the same reasons and for aesthetic reasons. While most of the elements of the illustrative embodiments of the anchors of this invention depicted in the drawings are functional, aspects of the shape and appearance of the illustrative embodiments are nonfunctional and ornamental.

The materials from which the components used in practicing this invention are made can be those described above as well as others, including materials not yet developed that have appropriate properties of strength, elasticity and the like that will be apparent to those skilled in the art in light of the foregoing. For instance, useful materials generally must be sterile or sterilizable and hypoallergenic. The illustrated components are typically intended to be reusable, but the invention could also be practiced using disposable components, such as, for instance, metal or plastic anchors supplied in a sterile package and optionally having pressure sensitive adhesive covered by a peel-off film on one surface of the anchor to protect the adhesive until the anchor is to be used.

The invention claimed is:

1. A method for stretching plastic tissue comprising:
   (a) evaluating the needed direction of stretching of the tissue;
   (b) determining a number of anchors to employ;
   (c) installing at least one anchor invasively into the tissue using prongs, sutures, flukes, or other invasive methods;
   (d) securing at least one elastomeric force applying component to the at least one anchor without knotting the force applying component;
   (e) adjusting tension by removing and re-securing the same at least one elastomeric force applying component to the at least one anchor.

2. The method of claim 1 wherein the installing the at least one anchor further comprises creating guide marks using a marking instrument.

3. The method of claim 1 further comprising dressing the area of application prior to securing the elastomeric force applying component.

4. The method of claim 1 wherein the elastomeric force applying component is at least one monostrand elastomer having two ends.

5. The method of claim 4 wherein the securing the elastomeric force applying component further comprises securing one end of the elastomer to a cleat in a first anchor, lacing the elastomer around a hook of a second anchor, and securing the other end of the elastomer to a cleat in a third anchor.

6. The method of claim 1 wherein the elastomeric force applying component further comprises a tension indication feature.

7. The method of claim 6 wherein the adjusting tension further comprises referring to a tension application table to determine extension needed to apply a desired force.

8. The method of claim 1 wherein the tension is infinitely adjustable within an elastic limit of the elastomeric force applying component.

9. The method of claim 1 wherein the elastomeric force applying component comprises at least two elastomers each having two ends.

10. The method of claim 9 wherein securing the elastomeric force applying component further comprises securing one end of each elastomer to a first anchor and securing the other end of each elastomer to a second anchor.

11. The method of claim 1 wherein the elastomeric force applying component is a suture.

12. The method of claim 1 wherein said securing the elastomeric force applying component further comprises securing a first end of the elastomeric force applying component to a first anchor and securing a second end of the elastomeric force applying component to a second anchor.

13. The method of claim 1 wherein the at least one anchor further comprises a cleat for securing the force applying component.

14. The method of claim 1 wherein the at least one anchor further comprises a hook for engaging the elastomeric force applying component.

15. The method of claim 1 wherein the at least one anchor further comprises an eye.

\* \* \* \* \*